United States Patent [19]

Pyun et al.

[11] Patent Number: 5,900,434
[45] Date of Patent: May 4, 1999

[54] METHOD FOR INHIBITING THE PRODUCTION OF INTERLEUKIN-1 OR TUMOR NECROSIS FACTOR-α BY ADMINISTERING ACANTHOIC ACID

[75] Inventors: Kwang-Ho Pyun, Seoul; Inpyo Choi, Taejon; Hyung-Sik Kang, Taejon; Jung-Joon Lee, Taejon; Young-Ho Kim, Taejon, all of Rep. of Korea

[73] Assignee: Korea Institute of Science and Technology, Seoul, Rep. of Korea

[21] Appl. No.: 08/750,459

[22] PCT Filed: Jun. 7, 1995

[86] PCT No.: PCT/KR95/00074

§ 371 Date: Dec. 6, 1996

§ 102(e) Date: Dec. 6, 1996

[87] PCT Pub. No.: WO95/34300

PCT Pub. Date: Dec. 21, 1995

[30] Foreign Application Priority Data

Jun. 13, 1994 [KR] Rep. of Korea ............... 94-13209

[51] Int. Cl.⁶ ............... A61K 31/19; A61K 35/78
[52] U.S. Cl. ............... 514/557; 424/195.1; 514/826; 514/838; 514/885
[58] Field of Search ............... 424/195.1; 514/885, 514/838, 826, 765, 557

[56] References Cited

U.S. PATENT DOCUMENTS 5,378,466 1/1995 Endo ............... 424/195.1

OTHER PUBLICATIONS

Kim et al., Pimaradiene diterpenes from Acanthopanax Koreanum, J. Natural Products, 51:1080–1083, 1988.

Okuyama et al., Analgesic principles from Aralia Cordata Thunb., Chem. Pharm. Bull. 39:405–407, 1991.

The Merck Manual of Diagnosis and Therapy, vol. 1, General Medicine, 15th Ed., pp. 3, 48, 49, 524, 525, 654, 655, 661, 957, 1987.

Alberts et al., Molecular Biology Of The Cell, Garland Publishing, Inc., NY, NY, p. 695, 1983.

Holgate et al., Allergy, Raven Press Ltd., NY, NY, pp. 3.1–3.10 and 10.1–10.14, 1993.

*Primary Examiner*—Michael G. Wityshyn
*Assistant Examiner*—Janet M. Kerr
*Attorney, Agent, or Firm*—Anderson, Kill & Olick, P.C.

[57] ABSTRACT

Process for the preparation of (−)-pimara-9(11),15-diene-19-oic acid(acanthoic acid) and pharmaceutical compositions comprising acanthoic acid useful for the treatment of diseases caused by an excessive production of interleukin-1 or tumor necrosis factor-α.

3 Claims, 17 Drawing Sheets

METHOD FOR INHIBITING THE PRODUCTION OF INTERLEUKIN-1 OR TUMOR NECROSIS FACTOR-α BY ADMINISTERING ACANTHOIC ACID

FIELD OF THE INVENTION

The present invention relates to a process for the preparation of acanthoic acid((−)-pimara-9(11),15-diene-19-oic acid) and pharmaceutical compositions comprising same useful for the treatment of diseases caused by an excessive production of interleukin-1 (hereinafter, referred to as "IL-1") or tumor necrosis factor-α(hereinafter, referred to as "TNF-α").

BACKGROUND OF THE INVENTION

*Acanthopanax koreanum* Nakai (Araliaceae), which is found indigenously in Cheju Island, the Republic of Korea, has been used traditionally as remedies for neuralgia, paralysis, lumbago, etc. Various useful components, including acanthoic acid of the following formula (A), have been isolated from its root bark(Kim Y. H. and Chung, B. S., *J. Nat. Pro.*, 51, 1080(1988)).

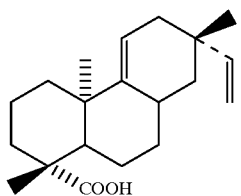

(A)

Acanthoic acid has been reported to have various pharmacological effects, e.g., analgesic and anti-inflammatory activity which is due to its ability to inhibit the leukocyte migration and prostaglandin $E_2(PGE_2)$ synthesis, and to exhibit very low toxicity, e.g., 1000 mg/kg of minimum lethal dose(MLD) when administered to a rat(Lee, Y. S., "Pharmacological Study for (−)-Pimara-9(11),15-Diene-19-oic Acid, A Component of *Acanthopanax koreanum* Nakai", doctorate thesis, Dept. of Pharmacy, Seoul National University, Korea, 1990).

As is well known, IL-1 is a regulatory factor which participates in a wide range of human defensive and immune mechanisms(see, e.g., Dinarello, D. A., *FASEB J.*, 2, 108 (1988)). IL-1, first discovered to be produced by activated macrophages, is produced and secreted by various cells, e.g., fibroblasts, keratinocytes, T cells, B cells, and astrocytes of brain; and has been reported to have various functions including: stimulating the proliferation of CD4+T cells (Mizel, S. B., *Immunol. Rev.*, 63, 51(1982)); stimulating the cell-killing effect of thymic $T_c$ cells through its binding to a T cell receptor(TCR)(McConkey, D. J., et al.,*J. Biol. Chem.*, 265, 3009(1990)); inducing the production of various materials participating in the inflammatory mechanisms, e.g., $PGE_2$, phospholipase $A_2(PLA_2)$, and collagenase(Dejana, E., et al., *Bolid*, 69, 695–699 (1987)); inducing the production of acute-phase proteins in liver(Andus, T., et al., *Eur. J. Immunol.*, 123, 2928(1988)); raising blood pressure in the vascular system(Okusawa, S., et al., *J. Clin. Invest.*, 81, 1162(1988)); inducing the production of other cytokines, e.g., IL-6 and TNF(Dinarello, C. A., et al.,*J. Immunol.*, 139, 1902(1987)), etc.

As has been reported, IL-1 relates to various immune diseases, e.g., rheumatoid arthritis(Nouri, A. M., et al., *Clin. Exp. Immunol.*, 58, 402(1984)), rejection mechanisms after the kidney transplantation(Mauri and Teppo, *Transplantation*, 45, 143(1988)), and septicemia(Cannon, J. G., et al., *Lymphokine Res.*, 7, 457(1988)). IL-1 has been also reported to induce a fever and pain when administered in a large amount to a human body(Smith, J., et al.,*Am. Soc. Clin. Oncol.*, 9, 710(1990)).

TNF-α, first discovered in a serum of an animal treated with BCG(Bacille Calmette-Guérin) or LPS (lipopolysaccharide) (Carswell, E. A., et al., *Proc. Natl. Acad. Sci. U.S.A.*, 72, 3666(1975)), has been reported to be produced by various cells, e.g., activated macrophages and fibroblasts. Further, TNF-α has been reported to have the functions of: killing the fibrosarcoma L929 cells(Espevik and Nissen-Meyer, *J. Immunol. Methods*, 95, 99(1986)); stimulating the proliferation of fibroblasts(Sugarman, B. J., et al., *Science*, 230, 943(1985)); inducing the production of $PGE_2$, arachidonic acid, etc. which may be involved in inflammatory responses(Suttys, et al.,*Eur. J. Biochem.*, 195, 465(1991)); inducing the production of IL-6 or other growth factors(Van Hinsbergh, et al., *Blood*, 72, 1467(1988)), etc.

TNF-α has been also reported to participate, directly or indirectly, in various diseases; and examples of said diseases are: infectious diseases carried by trypanosoma, strains of the genus Plasmodium, etc.(Cerami, A., et al., *Immunol. Today*, 9, 28(1988)); autoimmune diseases such as systemic lupus erythematosus(SLE) and arthritis(Fiers, W., *FEBS*, 285, 199(1991)); AIDS(Mintz, M., et al.,*Am. J. Dis. Child.*, 143, 771(1989)); septicemia(Tracey, K. J., et al., *Curr. Opin. Immunol.*, 1, 454(1989)); and infections (Balkwill, F. R. 1989, *Cytokines in Cancer Therapy*, Oxford University Press).

These observations have buttressed the importance of regulating the production of IL-1 and TNF-α for the maintenance of the homeostasis of immune system in a human body and for the treatment and prophylaxis of related diseases.

Accordingly, there have been proposed numerous approaches to regulate the production of interleukins. For instance, it has been reported that the occurrence of septicemia, arthritis, inflammations, etc. in animal models can be decreased by the inhibition of IL-1 binding to its receptors by employing naturally occurring IL-1 receptor inhibitors(IL-1 Ra)(Dinarello, C. A. and Thompson, R. C., *Immunol. Today*, 12, 404(1991)), and there have been proposed certain methods for inhibiting the activity of IL-1 by employing particular antibodies(Giovine, D. F. S. and Duff, G. W., *Immunol. Today*, 11, 13(1990)). In case of IL-6, proliferation of myelocytes in a patient suffering from myeloma which is caused by an excessive secretion of IL-6 has been suppressed by employing antibodies against IL-6 or IL-6 receptor(Suzuki, H., *Eur. J. Immuno.*, 22, 1989 (1992)).

However, no substance or method has been reported to inhibit specifically the productions of IL-1 and TNF-α and, therefore, efforts have continued for the discovery of specific inhibitors against the production of IL-1 and TNF-α.

SUMMARY OF THE INVENTION

Accordingly, it is an object of the present invention to provide a process for the preparation of acanthoic acid from root bark of *Acanthopanax koreanum* Nakai.

Another object of the present invention is to provide a pharmaceutical composition comprising a therapeutically effective amount of acanthoic acid and a pharmaceutically acceptable carrier, which is useful for the treatment of immune diseases caused by an excessive production of IL-1 or TNF-α.

BRIEF DESCRIPTION OF THE DRAWINGS

The above and other objects and features of the present invention will become apparent from the following description of the invention taken in conjunction with the accompanying drawings, in which.

DETAILED DESCRIPTION OF THE INVENTION

Figure 1:
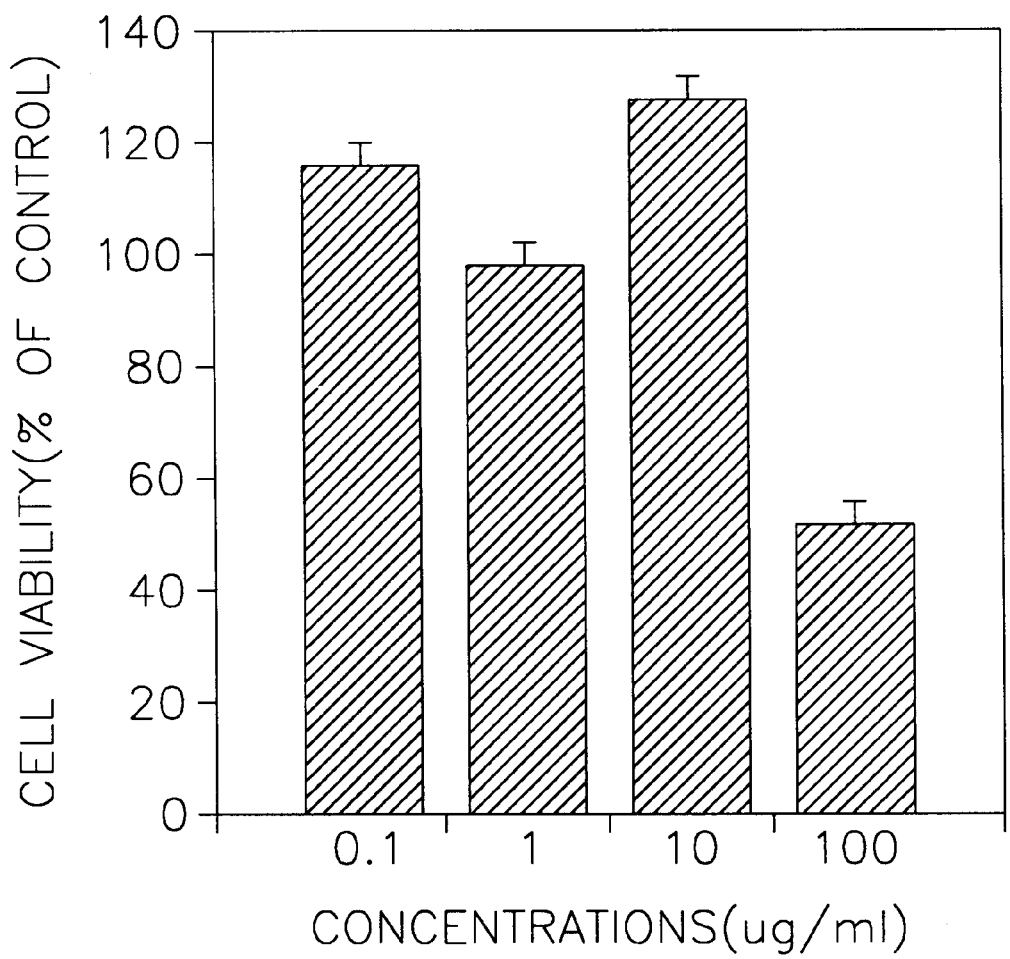
FIG. 1 shows the cytotoxicity of acanthoic acid on human monocytes and macrophages.

All references cited herein are hereby incorporated in their entirety by reference.

In accordance with the present invention, it has been found that acanthoic acid extracted from *Acanthopanax koreanum* Nakai possesses the ability to specifically inhibit the production of IL-1 or TNF-α; and, therefore, a pharmaceutical composition comprising an effective amount of acanthoic acid is useful for the treatment of various immune diseases caused by an excessive production of IL-1 or TNF-α.

Said acanthoic acid may be extracted from the root bark of *A. koreanum* Nakai by employing various organic solvents, e.g., methanol, diethyl ether, or a mixture thereof, etc. Especially, acanthoic acid may be prepared in accordance with the following preferred embodiment of the present invention.

To 1 kg of dried root bark of *A. koreanum* Nakai is added 1 to 3 l, preferably 2 l of methanol; and the mixture is heated at a temperature ranging from 20 to 60° C., preferably, at a room temperature, for at least 10 hours, preferably, for 12 hours, and filtered. Said procedure is repeated, preferably three times, and the combined filtrates are concentrated under a reduced pressure to obtain a methanol extract.

100 g of said methanol extract is partitioned with 200 to 400 ml, preferably 300 ml, of water and 200 to 400 ml, preferably 300 ml, of diethyl ether. The diethyl ether fraction is separated therefrom and then concentrated under a reduced pressure to obtain a diethyl ether extract. Said extract is purified by a silica gel column chromatography using a mixture of hexane and ethyl acetate as an eluent to obtain acanthoic acid.

Said acanthoic acid exhibits anti-inflammatory and anti-fibrogenic effects, inhibits the synthesis of collagen and the production of the reactive oxygen species, and reduces GOT and GPT levels in serum. That is, it can be employed in a pharmaceutical composition for the treatment of immune diseases caused by an excessive production of IL-1 or TNF-α, e.g., septicemia, rheumatoid arthritis, inflammation, hepatocirrhosis and silicosis.

The pharmaceutical compositions of the present invention may comprise pharmaceutically acceptable excipients, carriers or diluents in addition to acanthoic acid as an active ingredient. The pharmaceutical formulations may be prepared in accordance with any of the conventional procedures.

In preparing the compositions, the active ingredient is preferably admixed or diluted with a carrier, or enclosed within a carrier, which may be in the form of a capsule, sachet or other container. When the carrier serves as a diluent, it may be a solid, semi-solid or liquid material acting as a vehicle, excipient or medium for the active ingredient. Thus, the compositions may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starch, gum acacia, alginate, calcium phosphate, calcium silicate, gelatin, cellulose, methyl cellulose, microcrystalline cellulose, polyvinylpyrrolidone, water, methylhydroxybenzoate, propylhydroxybenzoate, talc, magnesium stearate and mineral oil.

The formulations may additionally include lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

The pharmaceutical compositions can be administered by a variety of routes including oral, transdermal, subcutaneous, intravenous and intramuscular introduction. A typical daily dose of the active ingredient may range from about 1 to 500 μg/kg body weight, preferably 30 to 300 μg/kg body weight, and can be administered in a single dose or in divided doses. However, it should be understood that the amount of the active ingredient actually administered ought to be determined in light of various relevant factors including the condition to be treated, the chosen route of administration, the age and weight of the individual patient, and the severity of the patient's symptom; and, therefore, the above dose should not be construed to limit the scope of the invention in any way.

The following Preparation Example and Examples are intended to further illustrate the present invention without limiting its scope; and the experimental methods used in the Examples can be practiced in accordance with the Reference Examples given herein below, unless otherwise stated.

Further, percentages given below for solid in solid mixture, liquid in liquid, and solid in liquid are on a wt/wt, vol/vol and wt/vol basis, respectively, unless specifically indicated otherwise.

PREPARATION EXAMPLE

Preparation of Acanthoic Acid

About 1.7 kg of well-dried root bark of *A. koreanum* Nakai was chopped and extracted with about 4 l of methanol at a room temperature for 24 hours, and then filtered. The extraction procedure was repeated three times and the combined filtrates were concentrated under a reduced pressure to obtain about 200 g of the methanol extract.

All of said methanol extract was partitioned with 600 ml of distilled water and 600 ml of diethyl ether. Diethyl ether layer was separated and concentrated under a reduced pressure to obtain 110 g of diethyl ether extract.

All of said diethyl ether extract was purified by a silica gel column chromatography using hexane:ethyl acetate (20:1(v/v)→5:1(v/v)) to obtain about 30 g of active material in a yield of 1.76%.

The active material was identified as acanthoic acid by using thin layer chromatography(TLC) compared with the standard(Kim, Y. H. and Chung, B. S., *J. Nat. Pro.*, 51, 1080(1988)), and this was also confirmed by $^1$H-NMR, $^{13}$C-NMR, MS and IR.

REFERENCE EXAMPLE 1

Separation of Cells for Assay (1) Separation of human monocytes, macrophages and neutrophils Normal human peripheral blood was heparin-treated and diluted with equal amount of Hank's balanced salt solution (HBSS: $Ca^{2+}$ and $Mg^{2+}$ free). The diluted blood was put into a centrifuge tube containing therein Ficoll-Hypaque(Sigma, St. Louis, Mo., U.S.A.) layer having a density of 1.077 piled up on Ficoll-Hypaque layer having a density of 1.119, and then centrifuged at 700×g for 30 minutes to obtain monocytes from the layer between Ficoll-Hypaque layer having a density of 1.077 and serum layer, and neutrophils from the layer between Ficoll-Hypaque layer having a density of 1.077 and that having a density of 1.119. The separated cells were washed twice with 4° C. HBSS($Ca^{2+}$ and $Mg^{2+}$ free) and suspended in RPMI 1640 medium(Gibco, Grand Island, N.Y., U.S.A.) containing 10% fetal bovine serum(FBS, Hyclone, Logan, Utah, U.S.A.). The suspensions were added to the wells of 24-well incubation plate(Costar, Cambridge, Mass., U.S.A.) and incubated at 37° C. for 2 hours to obtain monocytes, macrophages and neutrophils.

(2) Separation of fibroblasts

Fibroblasts were separated from rats by using a modification of the method of Phan, S. H., et al. described in *J. Clin. Invest.*, 76, 241(1985), as follows.

A rat was anesthetized with ether and its lungs were isolated on the aseptic worktable. The lungs were cut into small pieces in the size ranging from 2 to 4 mm and suspended in phosphate buffered saline(PBS) containing collagenase and 0.5% trypsin to digest the tissues at 37° C. for 2 hours. The suspension was filtered through sterilized gauze to remove undigested tissues, etc. The separated cells were washed with PBS twice or three times and suspended into RPMI 1640 medium(Gibco, Grand Island, N.Y., U.S.A.) containing 10% fetal bovine serum(FBS, Hyclone, Logan, Utah, U.S.A.). The suspension was added to the wells of incubation plate and incubated at 37° C. for 1 to 2 days in 5% $CO_2$ incubator (Lunaire Environ, Inc., Pa., U.S.A.). The plate was washed with RPMI 1640 medium to remove the cells which did not adhere to the plate. Fresh medium was added to the plate and the incubation was continued until the confluent layer was formed. The cells undergone subcultures less than 5 times were used in the following tests.

NIH3T3 fibroblast(ATCC CRL 1658) was cultured in RPMI 1640 medium containing 10% FBS under the same conditions as described above.

(3) Treatment of cells with acanthoic acid

Acanthoic acid was added in various concentrations to $5\times10^5$/ml of cells obtained in the above procedures, and the cells were precultured at 37° C. for 1 hour in 5% $CO_2$ incubator. Then, 1 ml each of silica(100 μg/ml) and RPMI 1640 medium containing 2% FBS were added thereto and the cells were cultured under the same conditions as above for 48 hours. The culture supernatant was collected and centrifuged at 1,500 rpm for 10 minutes to remove the cells and silica. The obtained supernatant was dialyzed against PBS and filtered by 0.2 μm filtration syringe, and the filtrate was stored at −20° C.

REFERENCE EXAMPLE 2

Assay for Cytotoxicity of Acanthoic Acid

The cytotoxicity of acanthoic acid was determined by the following procedures.

According to the procedures of Reference Example 1 (3), $5\times10^5$ cells/ml each of monocytes and macrophages obtained in Reference Example 1 (1) were treated with 0.1, 1, 10 or 100 μg/ml of acanthoic acid obtained in the Preparation Example and incubated under the same conditions. In accordance with the method of Alley, M. C., et al. described in *Cancer Res.*, 48, 589(1988), each culture was added to the wells of the incubation plate in an amount of 1 ml/well, and 0.5 mg of 3-4,5-dimethylthiazol-2,5-diphenyltetrazolium bromide(MTT, Sigma) was added to each of the wells. After incubating at 37° C. for 4 hours, the culture was centrifuged to remove supernatant. 100 μl each of acidified isopropanol(0.04N HCl in isopropanol) was added to the cells in each well to elute formazan produced by the living cells, and optical density (O.D.) was determined at 540 nm by using an ELISA reader (Titertek multiskan Mcc/340)(FIG. 1).

FIG. 1 shows the relative values of optical density of the sample with respect to the concentration of acanthoic acid when the optical density of the control group which was not treated with acanthoic acid is regarded as 100%. When the survival rate of monocyte and macrophage decreases due to the toxicity of acanthoic acid, the production of formazan also decreases, which causes the optical density to decrease. The samples treated with acanthoic acid show no significant difference from the control group until the concentration of acanthoic acid reaches 10 μg/ml. Therefore, it is confirmed that acanthoic acid has no cytotoxicity at the concentration lower than 10 μg/ml and, hereinafter, all the tests were carried out in this concentration range.

EXAMPLE 1

Inhibition of IL-1 Production in Human Monocytes and Macrophages by Acanthoic Acid The monocytes and macrophages obtained in Reference Example 1 (1) were incubated with 0.1 to 100 μg/ml of acanthoic acid for an hour and treated with 100 μg/ml of silica for 48 hours. The culture was centrifuged to obtain supernatant, which was then dialyzed against PBS. The activity of IL-1 in the dialyzate was determined in accordance with the method of Gery described in *Cellular Immunology*, 64, 293–303(1981) as follows.

$1\times10^7$ cells/ml of C3H/HeJ mouse thymocytes suspended in RPMI 1640 medium containing 10% FBS were treated with 1 μg/ml of phytohemagglutinin(PHA, Burroughs Wellcome, Research Triangle Park, N.C., U.S.A.) and 100 μl each of the suspensions was added to the wells of 96-well incubation plate(Costar, plat-bottomed). 50 μl of said dialyzate and RPMI 1640 medium containing 10% FBS were added to each of the wells. Then, the plate was incubated at 37° C. under 5% $CO_2$ for 72 hours. At 16 hours before the completion of the incubation, 0.5 μCi/well of $^3$H-thymidine was added to the wells. When the incubation was completed, the cells were collected on the glass fiber filter and the amount of incorporated $^3$H-thymidine was determined by liquid scintillation counter(Beckman).

Figure 2:
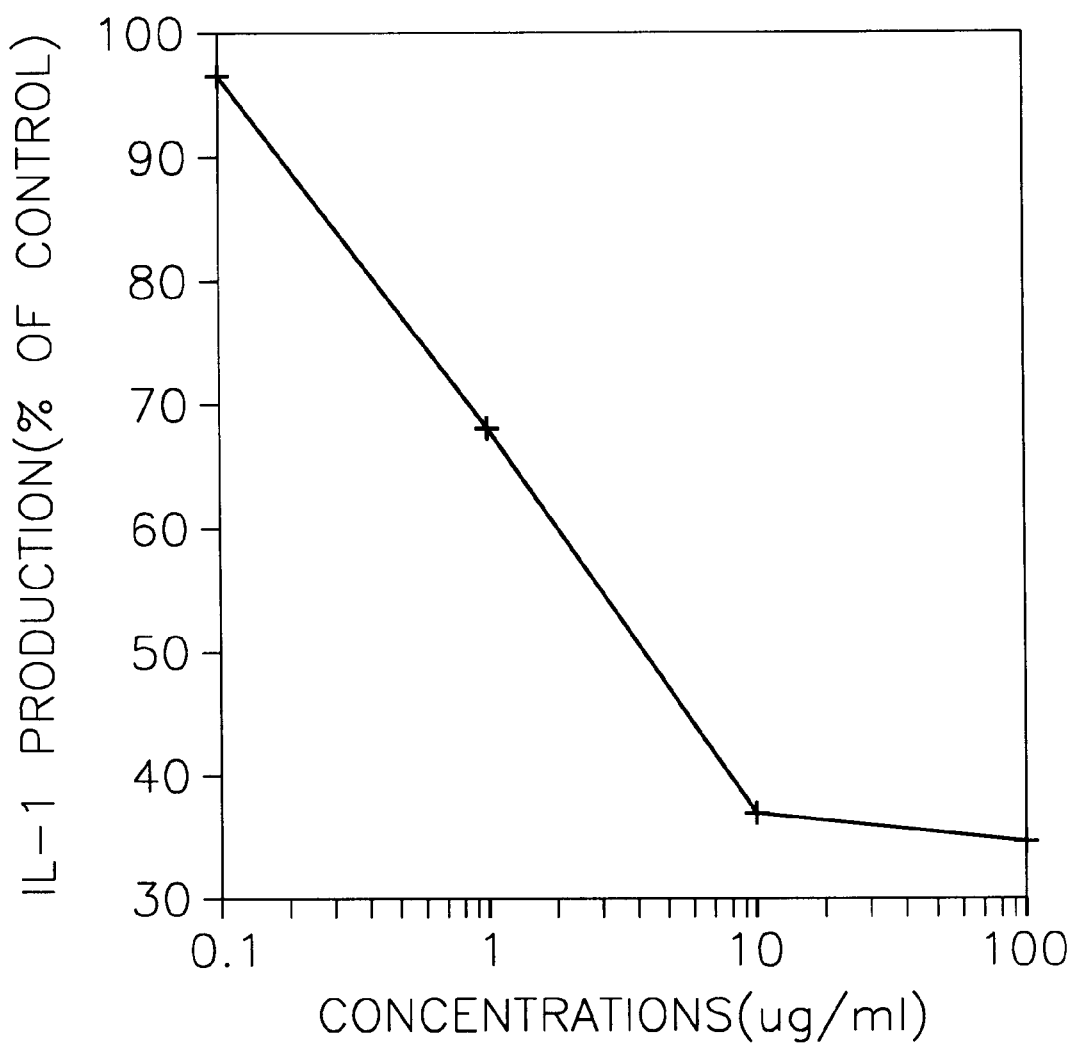
FIG. 2 depicts the inhibitory effect of acanthoic acid on the production of IL-1 in human monocytes and macrophages.

FIG. 2 shows relative values of the amount of incorporated $^3$H-thymidine with respect to the concentration of acanthoic acid when the amount of incorporated $^3$H-thymidine of the control group which was not treated with acanthoic acid is regarded as 100%. As can be seen from FIG. 2, the productions of IL-1 in human monocytes and macrophages were inhibited by acanthoic acid in a concentration-dependent mode.

EXAMPLE 2

Inhibition of TNF-α Production in Human Monocytes and Macrophages by Acanthoic Acid Human monocytes and macrophages were treated with acanthoic acid in accordance with the same procedures as in Example 1, and the activity of TNF-α was measured by cell lytic assay in accordance with the method of Aggarwal as described in *J. Biol. Chem.*, 260, 2345(1985).

TNF-α dependent L929 fibroblasts(ATCC CCL1) were suspended in RPMI 1640 medium containing 5% FBS and added to the wells of 96-well incubation plate in an amount of 3×10$^4$ cells/well. The plate was incubated at 37° C. for 2 hours to make the cells adhere to the incubation plate. Then, the medium was removed and 1 μg/ml of actinomycin D(Sigma) and 50 μl of culture dialyzate of monocytes and macrophages obtained in Example 1 were added to each of the wells. The final concentration of FBS in each well was adjusted to 5% and the cells were incubated at 37° C. under 5% $CO_2$ for 24 hours.

When the incubation was completed, the medium was removed and the cells were washed twice with PBS and stained for 5 minutes with 0.5% crystal violet solution in 20% methanol. The cells were washed three times with PBS and dried. Then, 100 μl of 33% acetic acid was added to each of the wells to release the dye, and then the O.D. of sample obtained from each of the wells was determined by using ELISA reader with 570 nm reading filter and 405 nm reference filter. The amount of released dye was calculated from the O.D. value with reference to that of the internal control group, i.e., rHu TNF-α(Genzyme).

Figure 3:
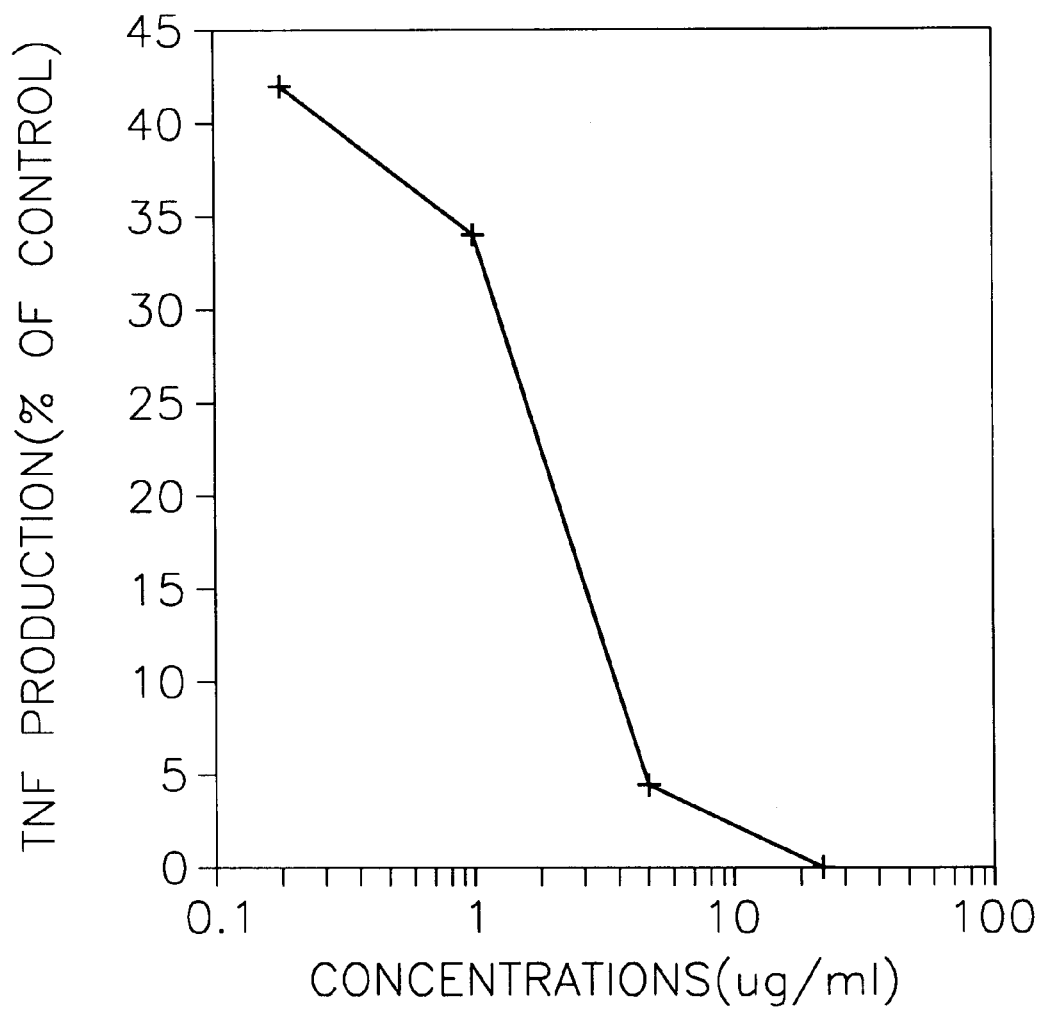
FIG. 3 provides the inhibitory effect of acanthoic acid on the production of TNF-α in human monocytes and macrophages.

As can be seen from FIG. 3, 5 μg/ml or more of acanthoic acid inhibits the production of TNF-α by at least 90%.

EXAMPLE 3

Inhibition of TNF-α Production in Rat Alveolar Macrophages and Lymphocytes by Acanthoic Acid A rat was anesthetized with ketamine and its alveolar macrophages and lymphocytes were obtained therefrom by inserting a sterilized thin tube into the branchia and repeating three times the injection and sucking out of 10 ml of RPMI 1640 medium with a 30 ml syringe. The obtained cells were centrifuged at 400×g for 5 minutes, suspended in 50 ml of RPMI 1640 medium containing 10% FBS and then incubated at 37° C. for 2 hours to adhere to the incubation plate. The plate was washed twice with PBS to remove floating cells and obtain alveolar macrophages and lymphocytes.

Each 2×10$^5$ cells/well of the alveolar macrophages and lymphocytes were added to the wells of 24-well incubation plate and 10 μg/ml of acanthoic acid was added to each of the wells. The cells were precultured at 37° C. for 1 hour and treated with 100 μg/ml of silica for 3 days. The culture was dialyzed against PBS and the activity of TNF-α in the dialyzate was determined by using TNF-α dependent L929 cell line in accordance with the procedure as described in Example 2.

Figure 4:
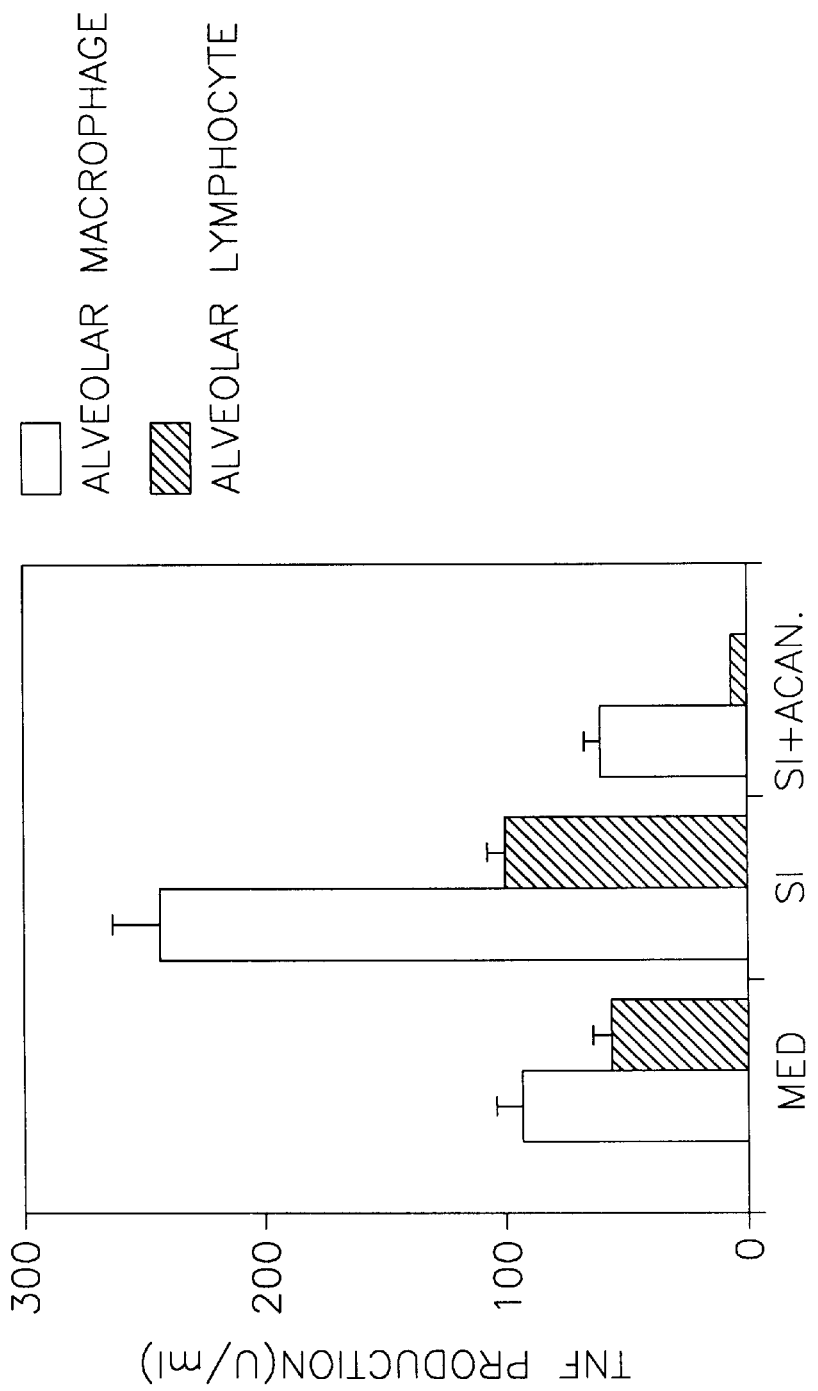
FIG. 4 offers the inhibitory effect of acanthoic acid on the production of TNF-α in rat alveolar macrophages and lymphocytes.

As can be seen from FIG. 4, it was observed that the production of TNF-α in rat alveolar macrophages and lymphocytes was also inhibited by acanthoic acid. In FIG. 4, med, Si and Si+acan. represent non-treated control group, silica-stimulated sample and acanthoic acid-treated and silica-stimulated sample, respectively.

EXAMPLE 4

Inhibition of Production of Reactive Oxygen Species by Acanthoic Acid

Inflammatory responses are known as a cascade reaction comprising the secretion of various cytokines, e.g., IL-1, from immune cells stimulated by various stimulants; production of phospholipase $A_2$, lysosomal enzyme, reactive oxygen species, etc. by other immune cells stimulated by said cytokines; and damage of tissues induced by the above products(Pruzanski, W. and Vadas, P., *Immunol. Today*, 12, 143(1991)). The ability of acanthoic acid to block the inflammatory reactions was tested by measuring their inhibitory activity to the production of reactive oxygen species, i.e., $H_2O_2$ and $O_2^-$.

The amount of $H_2O_2$ was determined by a microassay employing 96-well microplate as follows. 5×10$^5$ cells of neutrophils were added to each of the wells containing RPMI 1640 medium, and then 25 μl of horseradish peroxidase (500 μg/ml; type II, Sigma) and 75 μl of phenol red(1 mg/ml) were added to each of the wells. Thereafter, the cells were treated with 10, 20 and 50 μg/ml of acanthoic acid for an hour, stimulated with 10$^{-7}$ M phorbol myristate acetate (PMA) and then incubated at 37° C. for 60 minutes. When the incubation was completed, 3M NaOH was added to the wells in an amount of 25 μl/well to stop the reaction and O.D. was measured at 620 nm by using ELISA reader (Dynatech Lab. Inc.) to determine the change of colors with respect to the oxidation of phenol. The amount of $H_2O_2$ was determined by employing a standard curve prepared by diluted $H_2O_2$(Sigma).

For the purpose of measuring the amount of produced $O_2^-$, neutrophils suspended in RPMI 1640 medium in a concentration of 1×10$^6$ cells/800 μl was added to a part of the wells of 24-well plate and 10 μg/ml of superoxide dismutase(SOD, Sigma) was added to the empty wells. The plate was stored at 37° C. for 2 minutes, and cytochrome C(3 mg/ml, Sigma) was added to the wells in a concentration of 100 μl/well. The cells were treated with 10, 20 and 50 μg/ml of acanthoic acid for an hour and reacted at 37° C. for 20 minutes by introducing 10$^{-7}$ PMA as a stimulant. The reaction was terminated by adding 1 mM N-ethylmaleimide (Sigma) to the wells and the culture was centrifuged at 1,600×g for 10 minutes to obtain a supernatant. The change of color of the supernatant caused by the reduction of cytochrome C was measured at 550 nm by using a UV-Visible spectrophotometer (Kontron Instrument, Milano, Italy). The amount of produced $O_2^-$ was represented by the concentration of SOD which can suppress the reduction of cytochrome C in 1×10$^6$ cells for 20 minutes, by employing the extinction coefficient of cytochrome C($E_{550 nm}=1.83\times10^4 mM^{-1}cm^{-1}$).

As can be seen from Table I, 50 μg/ml of acanthoic acid inhibits the production of $H_2O_2$ by 85%, and the production of $O_2^-$ by 72%. The result shows that acanthoic acid has a strong inhibitory activity to the inflammatory response.

TABLE I

Inhibitory effect of acanthoic acid on the production of reactive oxygen species in human neutrophils

| Sample | Amount of produced reactive oxygen species (% to the control group) | |
|---|---|---|
| | $H_2O_2$(nM/60 min.) | $O_2^-$(nM/20 min.) |
| Medium only | 11.5(11.1) | 2.0(12.9) |
| PMA | 103.6(100) | 15.5(100) |
| PMA + Acanthoic acid | | |
| 10 μg/mλ | 72.6(70) | 11.9(76.8) |
| 20 μg/mλ | 38.7(37.4) | 4.9(31.6) |
| 50 μg/mλ | 16.4(15.8) | 4.4(28.4) |

Figure 5:
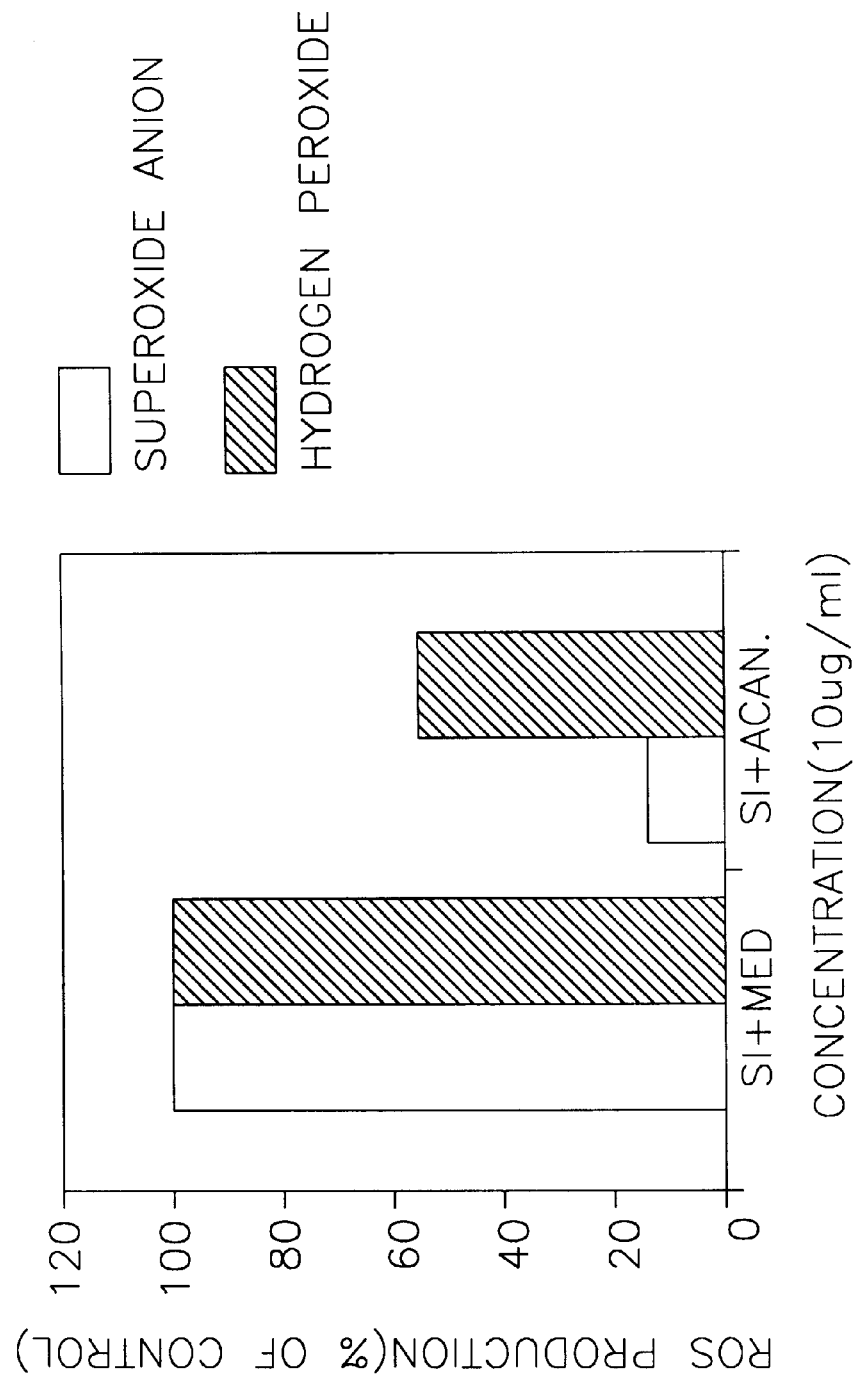
FIG. 5 presents the inhibitory effect of acanthoic acid on the production of the reactive oxygen species in human monocytes and macrophages.

On the other hand, the same procedures as above were repeated to determine the amount of $H_2O_2$ and $O_2^-$ produced by 5×10$^5$ cells of human monocytes and macrophages which was treated with 10 μg/ml of acanthoic acid at 37° C. for an hour and then stimulated by 100 μg/ml of silica. As can be seen from FIG. 5, the amounts of $H_2O_2$ and $O_2^-$ decrease significantly in the acanthoic acid-treated and silica-stimulated monocytes and macrophages(si+acan.) in contrast with the control group treated with only silica(si+med).

EXAMPLE 5

Inhibition of Proliferation of Fibroblasts by Acanthoic Acid

Figure 6:
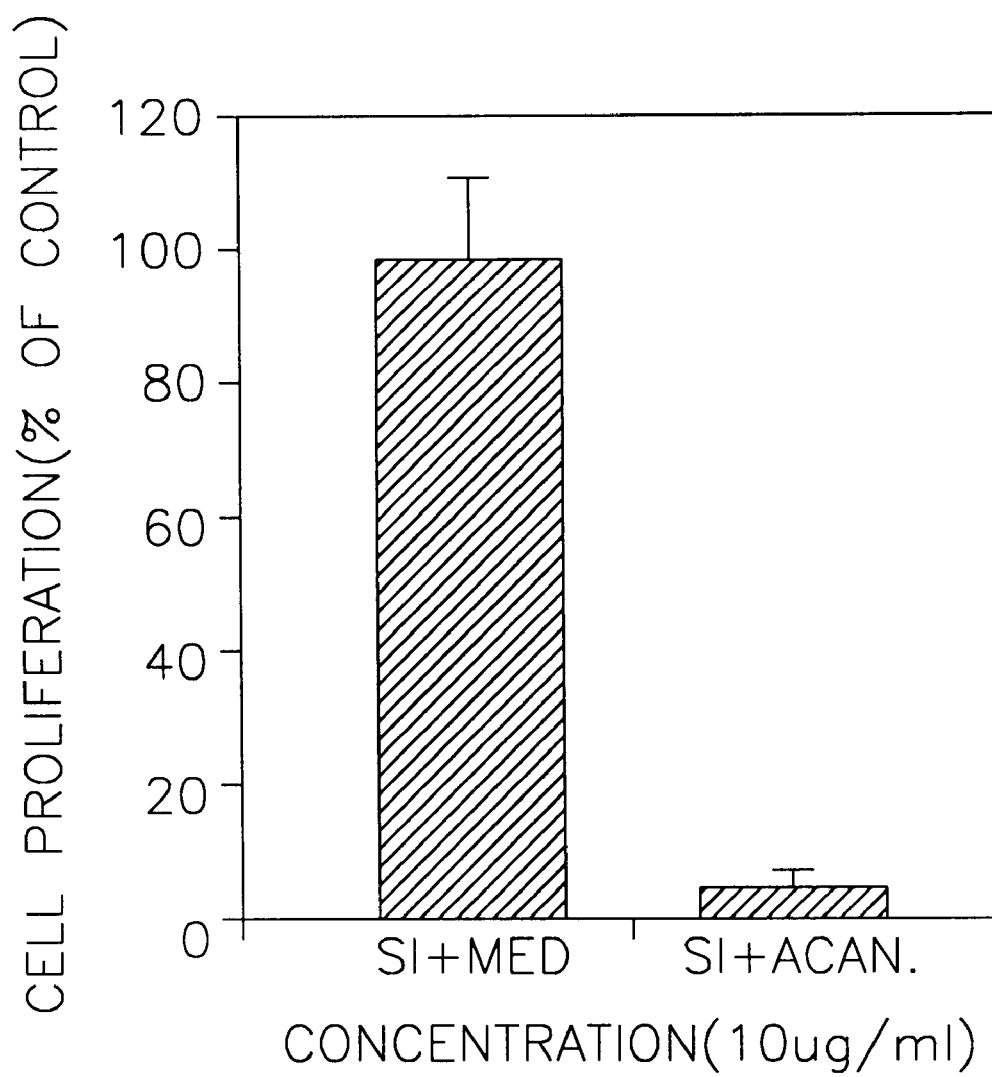
FIG. 6 illustrates the inhibitory effect of acanthoic acid on the proliferation of NIH3T3 fibroblasts.

Fibrosis is caused largely by the proliferation of fibroblasts or by the synthesis of collagen. To confirm the effect of acanthoic acid on the proliferation of fibroblasts, human monocytes and macrophages were treated with 10 μg/ml of acanthoic acid and cultured according to the procedure as described in Reference Example 1 (3). The culture was dialyzed against PBS, and 50 μl of the dialyzate was added to the wells of an incubation plate. 5×10$^3$ Cells of NIH3T3 fibroblasts(ATCC CRL 1658) were added to each of the wells and then cultured at 37° C. under 5% $CO_2$ for 5 days. After the addition of $^3$H-thymidine to the culture, the cells were cultured for additional 16 hours. The amount of $^3$H-thymidine incorporated in the cell was determined by employing liquid scintillation counter(FIG. 6). As can be seen from FIG. 6, the proliferation of fibroblasts is inhibited significantly in the acanthoic acid-treated and silica-stimulated fibroblasts (si+acan.) in contrast with the control group treated with only silica(si+med). It is supposed that such inhibition is caused by the action of acanthoic acid reducing the production of interleukins or other fibrogenic growth factors which cause fibrosis, or inducing anti-fibrogenic factors.

EXAMPLE 6

Inhibition of Collagen Synthesis by Acanthoic Acid

IL-1 and TNF-α are known as cytokines which cause fibrosis and induce collagen synthesis in rat fibroblast(Kang, H. S., et al., *Korean. J. Immunol.,* 14, 193(1992)). For the purpose of confirming the ability of acanthoic acid to suppress the action of IL-1 and TNF-α, its inhibitory effect on the collagen synthesis in rat pulmonary fibroblast and pulmonary tissues was determined. The amount of produced collagen in the culture of rat pulmonary fibroblast was measured by an indirect ELISA method, and that of pulmonary tissue was determined by measuring the concentration of hydroxyproline and calculating the amount of collagen therefrom by using the standard curve of internal control group.

To measure the amount of synthesized collagen in the culture of rat pulmonary fibroblast, collagen(Sigma, type I) as an internal control group was dissolved thoroughly in 1M acetic acid containing 1 mg/ml of pepsin, and the solution was serially diluted by 5-fold with coating buffer(0.05M carbonate, pH 9.6) in a concentration ranging from 1 μg to 16 pg. The diluted solutions were added to the wells of flat-bottomed microtiter plate(Dynatech, Immulon 2) in an amount of 100 μl/well.

On the other hand, 1 ml of the culture supernatant of rat pulmonary fibroblasts obtained in Reference Example 1 (2) was 10- to 20-fold concentrated by using speed vac dryer (Savant, Hicksville, N.Y., U.S.A.) and dissolved in 100 μl of coating buffer(0.1M NaHCO$_3$, 0.02% NaN$_3$; pH was adjusted to 9.6 with Na$_2$CO$_3$) and the solution was added to the wells in an amount of 100 μl/well and then coated at 4° C. overnight.

The plate was washed three times with washing buffer (PBS, 0.05% Tween 20, pH 7.4), and 1% bovine serum albumin(BSA, Sigma) was added to the wells in an amount of 100 μl/well. The plate was incubated at a room temperature for 2 hours to block the uncoated parts. The plate was washed four times with the same buffer as above, and alkaline phosphatase-conjugated rabbit anti-goat IgG (Cappel, Durham, N.C., U.S.A.), which was 1,000-fold diluted with a dilution buffer(0.05M Tris-HCl, 1 mM MgCl$_2$.6H$_2$O, 0.15M NaCl, 0.02% NaN$_3$, 1% BSA, 0.05% Tween 20, pH 8.1), was added to the wells in an amount of 100 μl/well.

The plate was incubated at 37° C. for 2 hours and then washed three times with the same buffer as above. To the wells was added 100 μl/well of p-nitrophenyl phosphate which was diluted with substrate buffer(0.05M NaHCO$_3$, 10 mM MgCl$_2$.6H$_2$O, pH 9.8) in a concentration of 1 mg/ml, and the O.D. of the culture was determined by using an ELISA reader at 405 nm. The amount of produced collagen was calculated from the O.D. value with reference to that of the internal control group.

Figure 7:
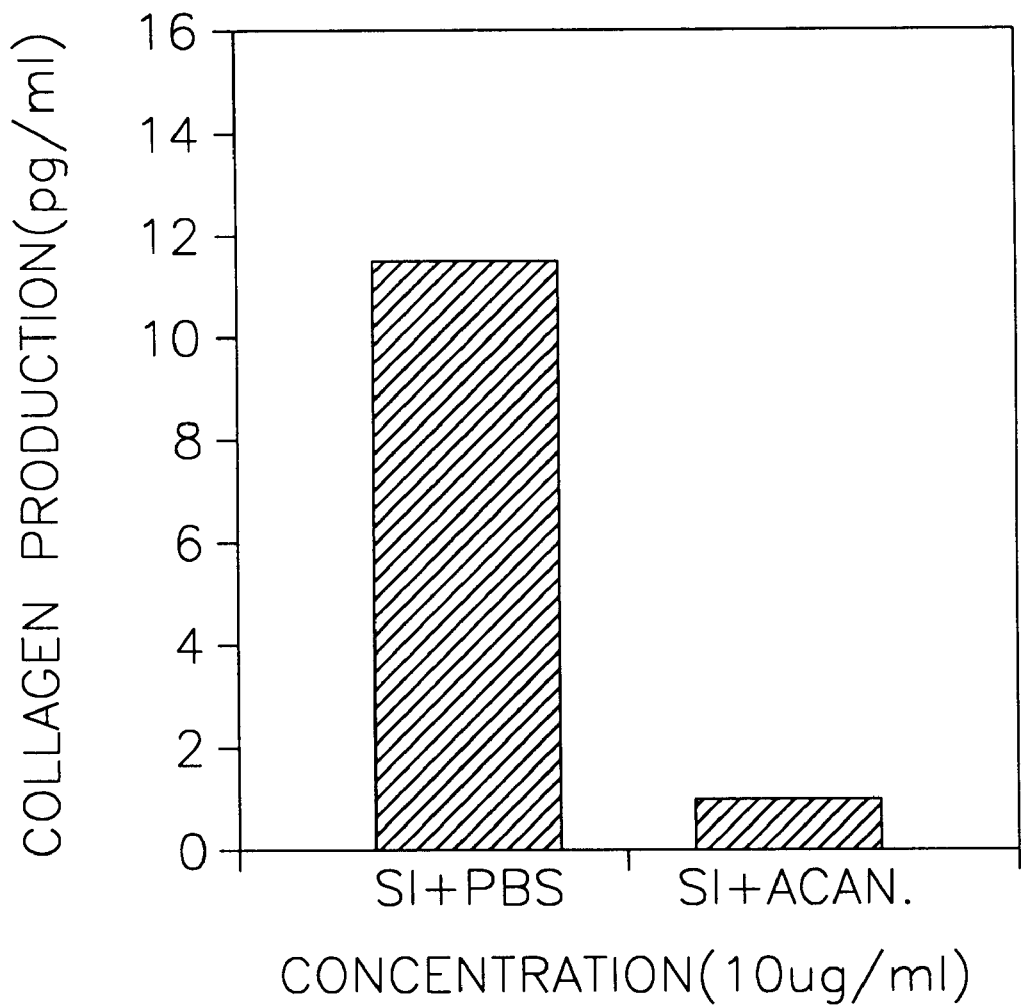
FIG. 7 displays the inhibitory effect of acanthoic acid on the production of collagen in rat pulmonary fibroblasts.

As can be seen from FIG. 7, the amount of synthesized collagen decreases significantly in the culture of rat pulmonary fibroblast which was pretreated with acanthoic acid. In FIG. 7, si+PBS and si+acan. represent silica-stimulated sample and acanthoic acid-treated and silica-stimulated sample, respectively.

Further, for the purpose of determining the amount of synthesized collagen in rat pulmonary tissues, the amount of hydroxyproline was measured as follows.

0.1 to 0.2 g of the rat pulmonary tissue was mixed with 1 ml of PBS and then crushed in a Pyrex tube(Corning, Rochester, N.Y., U.S.A.). The resulting tissue extract was ruptured by using an ultrasonicator(Heat system, W-380), 1 ml of hydrochloric acid was added thereto and the mixture was dried overnight at 120° C. in a drying oven. The resultant was freezed in a freezer, lyophilized in a freeze-dryer(Labconco) and dissolved completely in 1 ml of distilled water. 50 μl of the resulting solution was diluted with 50 μl of distilled water in a microcentrifuge tube. As an internal control group, trans-γ-hydroxy-L-proline(Sigma) was diluted in a concentration ranging from 20 μg to 150 pg, and 100 μl of each diluted solutions was added to the microcentrifuge tube. 0.9 ml of a solution prepared by dissolving 1.41 g of chloramine-T(sodium N-chloro-P-toluene sulfonamide) in a mixture of 10 ml of n-propanol and 10 ml of distilled water was added to the tube, which was stored at a room temperature for 20 minutes. Then, to the resulting mixture was added 1 ml of aldehyde/perchloric acid solution prepared by dissolving 15 g of p-dimethyl aminobenzaldehyde in 62 ml of n-propanol and then adding 26 ml of 60% perchloric acid thereto to make the total volume of 100 ml, and the resultant was mixed well. The microcentrifuge tube was reacted at 65° C. in a water bath for 15 minutes to develop colors. O.D. of the sample was measured at 650 nm, and the amount of hydroxyproline in the sample was calculated by employing the standard curve of internal control group.

Figure 8:
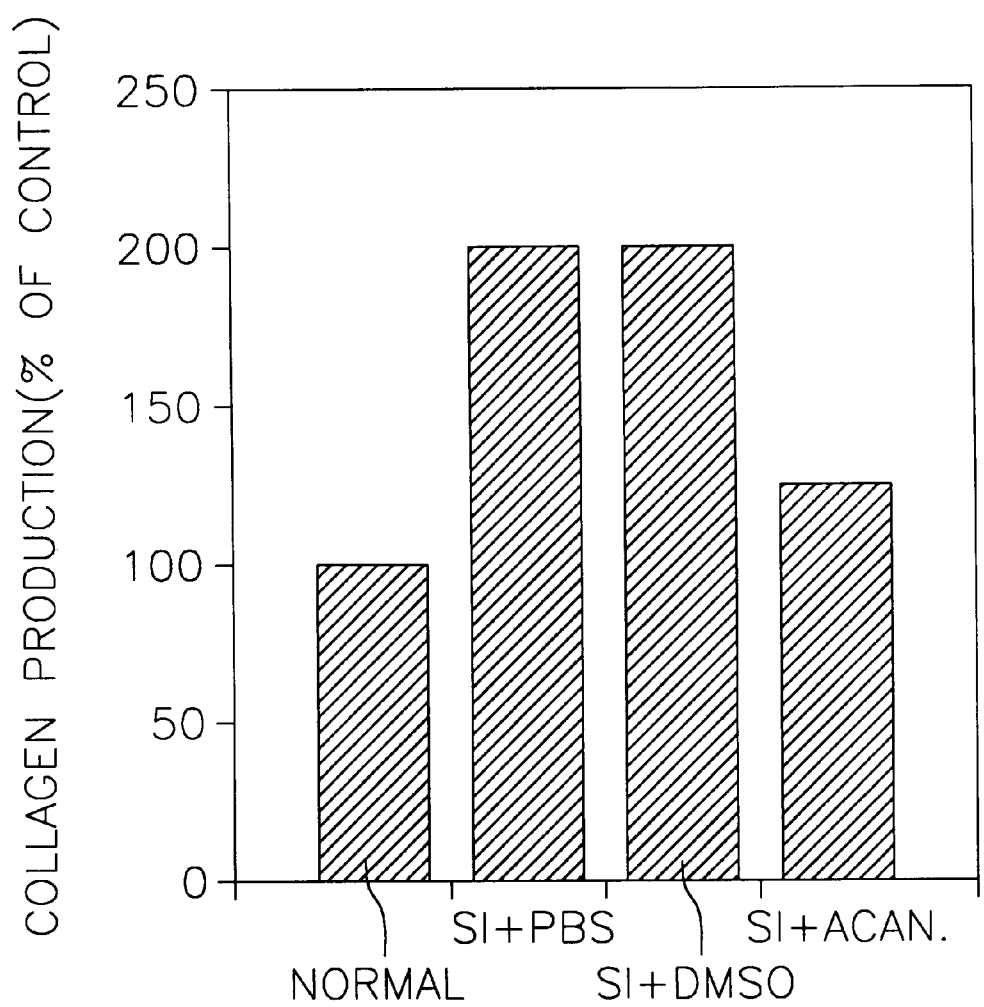
FIG. 8 exemplifies the inhibitory effect of acanthoic acid on the production of collagen in rat pulmonary tissues.

As can be seen from the result in FIG. 8, when the amount of collagen produced in normal rat pulmonary tissue (normal) is regarded as 100%, the amount of collagen synthesized in rat pulmonary tissue treated with silica only (si+PBS) or treated with silica and dimethylsulfoxide(si+DMSO) is remarkably high, while the amount of synthesized collagen decreases by about 50% in rat pulmonary tissue treated with silica, DMSO and acanthoic acid(si+acan.). The above result shows that acanthoic acid has anti-fibrogenic activity.

EXAMPLE 7

Inhibition of IL-6 production by Acanthoic Acid

For the purpose of confirming the in vivo anti-fibrogenic activity of acanthoic acid, an experimental silicosis model was established and the effect of acanthoic acid on the silicosis model when administered thereto was determined.

Silica was refined by removing any contaminant, e.g., $Fe_2O_3$, therefrom in accordance with the method of Lugano as described in *Am. J. Pathol.*, 109, 27–36(1982) as follows. Silica powder(Sigma, St. Louis, Mo.; the content of the particles having a diameter of 5 μm is at least 80%) was suspended in 1N HCl and the suspension was heated and washed with distilled water. The resultant was sterilized by dry heating at 200° C. for 2 hours and then used in the following experiment.

A 7 to 8 week-old male Sprague-Dawley rat and a 5-week old female ICR mouse were anesthetized by an intraperitoneal injection of 2 to 5 mg of ketamine chloride. The rat was injected into their bronchia with 50 mg of silica dissolved in 0.5 ml of sterilized PBS and the mouse was injected with 2 mg of silica dissolved in 0.1 ml of sterilized PBS, by using an 1 ml syringe. From the next day after the injection of silica, 10 mg of acanthoic acid was administered orally to the rat and mouse twice a week for a period ranging from 12 to 18 weeks.

Thereafter, the lungs of the rat and mouse were separated and fixed in 10% neutral formalin, spread out in 4 mm thickness and then embedded in paraffin in accordance with a conventional method. The embedded tissue was sectioned in 5 mm thickness, stained with hematoxylin eosin, Masson's trichrome and reticulin, and then observed under a microscope(FIG. 9).

Figure 9A:
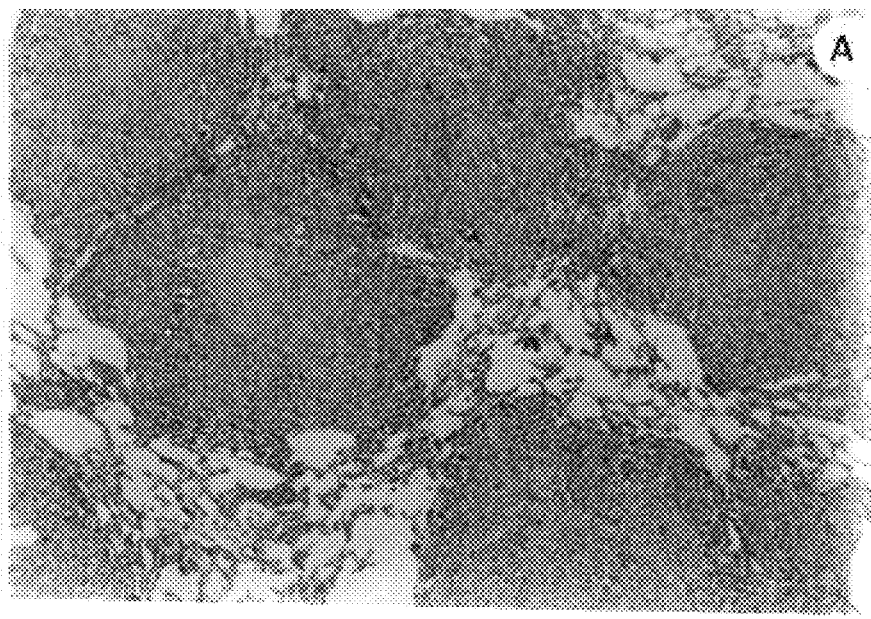
FIG. 9 exhibits the inhibitory effect of acanthoic acid on the silicosis in rat.
Figure 9B:
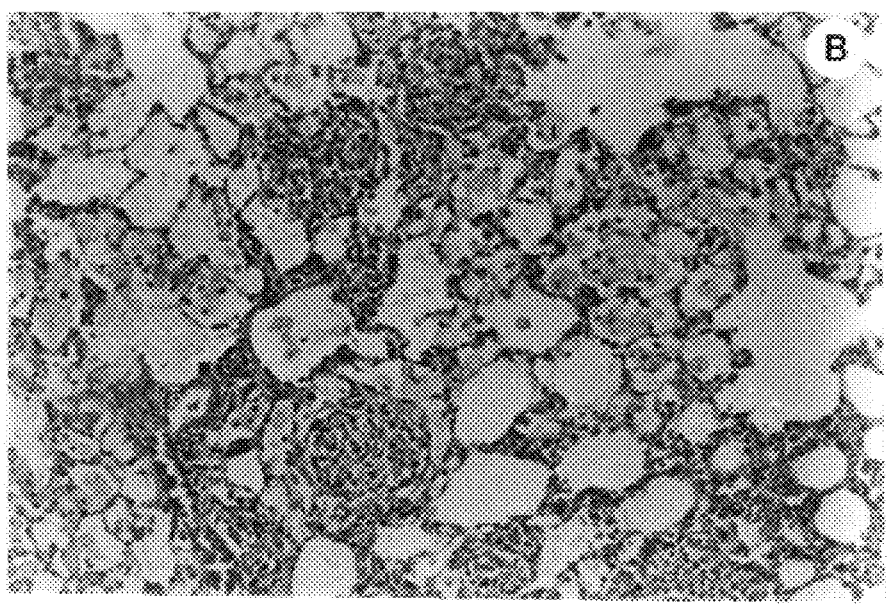

As can be seen from FIG. 9, in the lung of the rat administered with silica and DMSO(A), numerous coalescent granuloma showing excessive fibrosis and connective tissue formation, excessive monocyte infiltration, fibrosis and hyalinization are observed, while only small-sized granulomas which is not coalesce with each other and a slight fibrosis are observed in the lung of the rat administered with silica, DMSO and acanthoic acid(B). This result shows that acanthoic acid has an ability to inhibit the experimental silicosis.

EXAMPLE 8

Inhibition of Hepatocirrhosis by Acanthoic Acid

Hepatocirrhosis(hepatic sclerosis) is characterized by the fibrosis of whole liver, complete disruption of liver parenchyma by fibrous septa, and formation of regenerative nodules. It is derived mostly from a chronic hepatitis or chronic alcoholism, however, the precise causes thereof are unknown. In a hepatocirrhosis patient, the amount of cytokines, e.g., TNF-α, which is involved in inflammation and fibrosis, is in an increased state; and, therefore, the inhibition of hepatocirrhosis by acanthoic acid may be determined by the inhibitory activity to TNF-α.

To induce the experimental hepatocirrhosis in accordance with the method of Nakataukasa, H., et al. as described in *J. Clin. Invest.*, 85, 1833–1843(1990), 1.0 ml/100 g of body weight of $CCl_4$ solution(50% $CCl_4$+50% corn oil) was injected intraperitoneally to 4 week old male Sprague-Dawley rats twice a week, and 0.2 ml each of methanol extract of *A. koreanum* Nakai and acanthoic acid was administered orally at the time of the injection of $CCl_4$ twice a week. After 13 weeks from the start of the test, each of the rats was anesthetized with ether and the blood samples were obtained from the heart to determine serum glutamic-oxaloacetic transaminase(sGOT) value and serum glutamic-pyruvic transaminase(sGPT) value(FIG. 10).

Figure 10A:
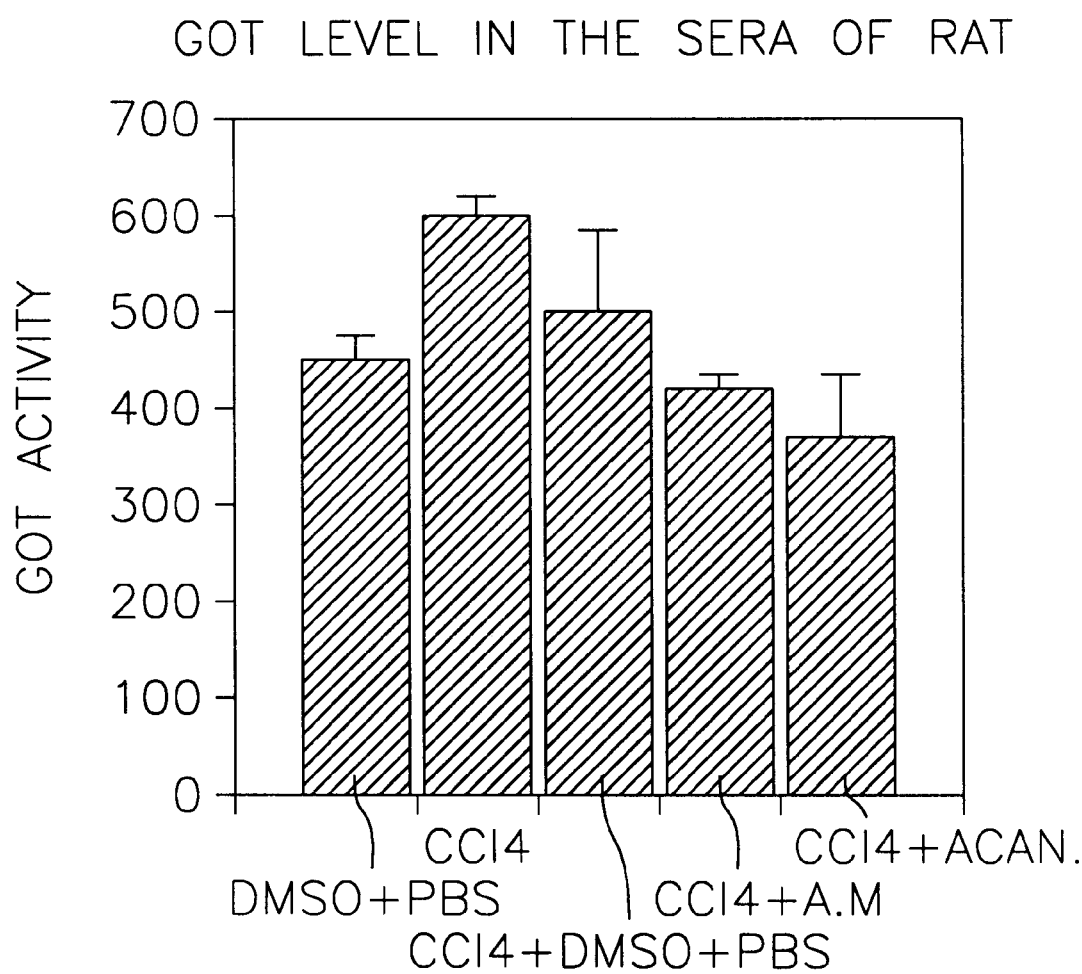
FIG. 10 demonstrates the effect of acanthoic acid on GOT and GPT level in serum of a rat suffered from induced hepatocirrhosis.
Figure 10B:
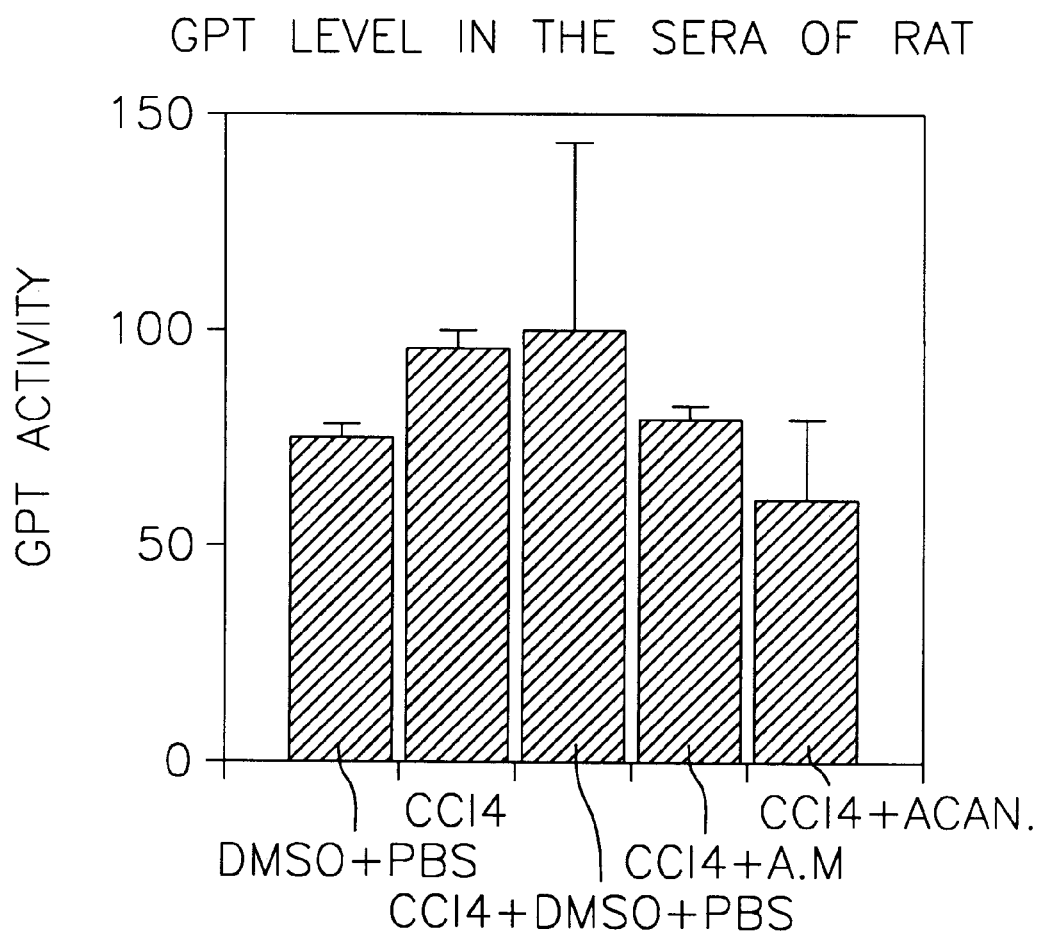
Figure 11A:
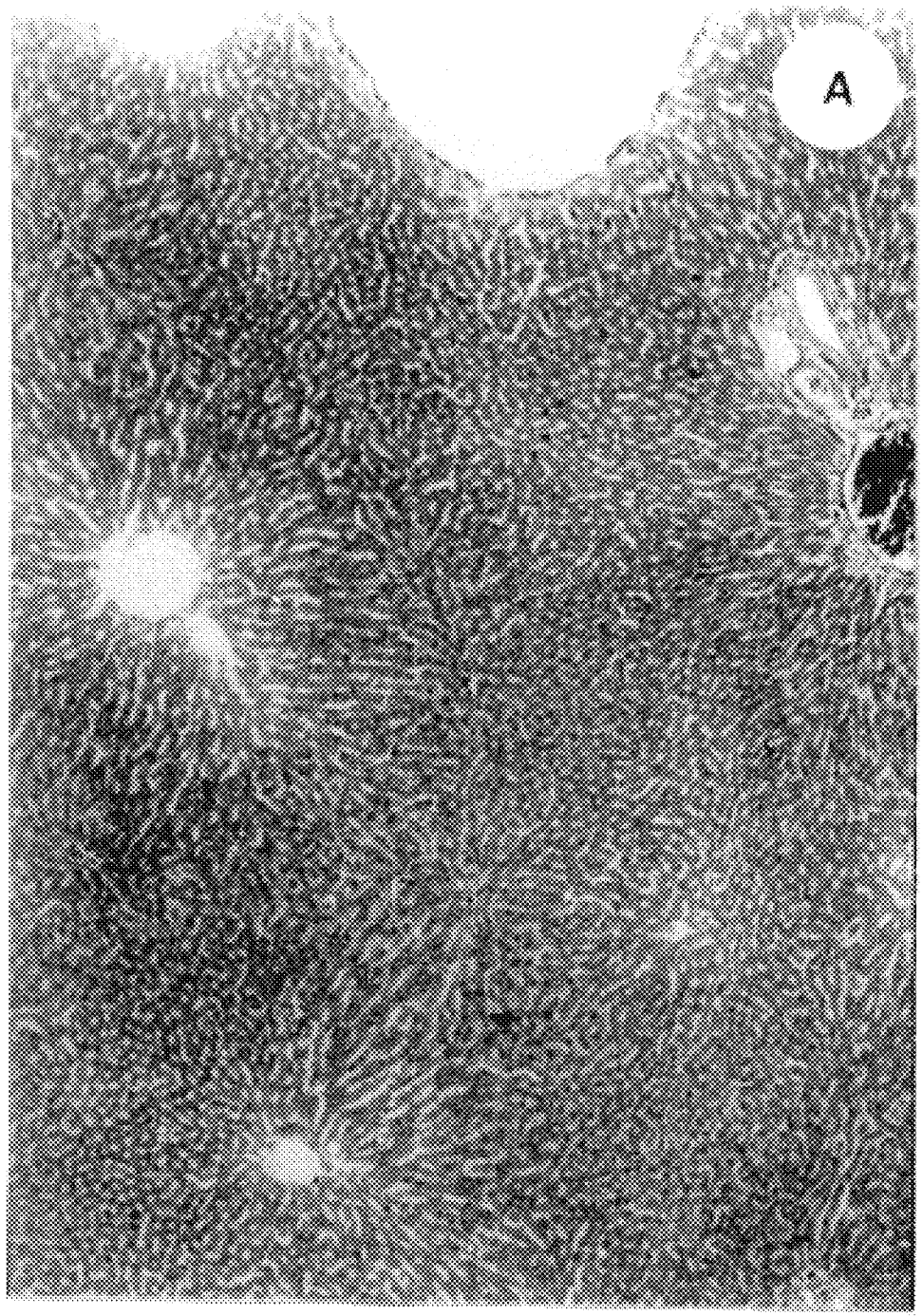
FIG. 11 highlights the effect of acanthoic acid on rat hepatocirrhosis.
Figure 11B:
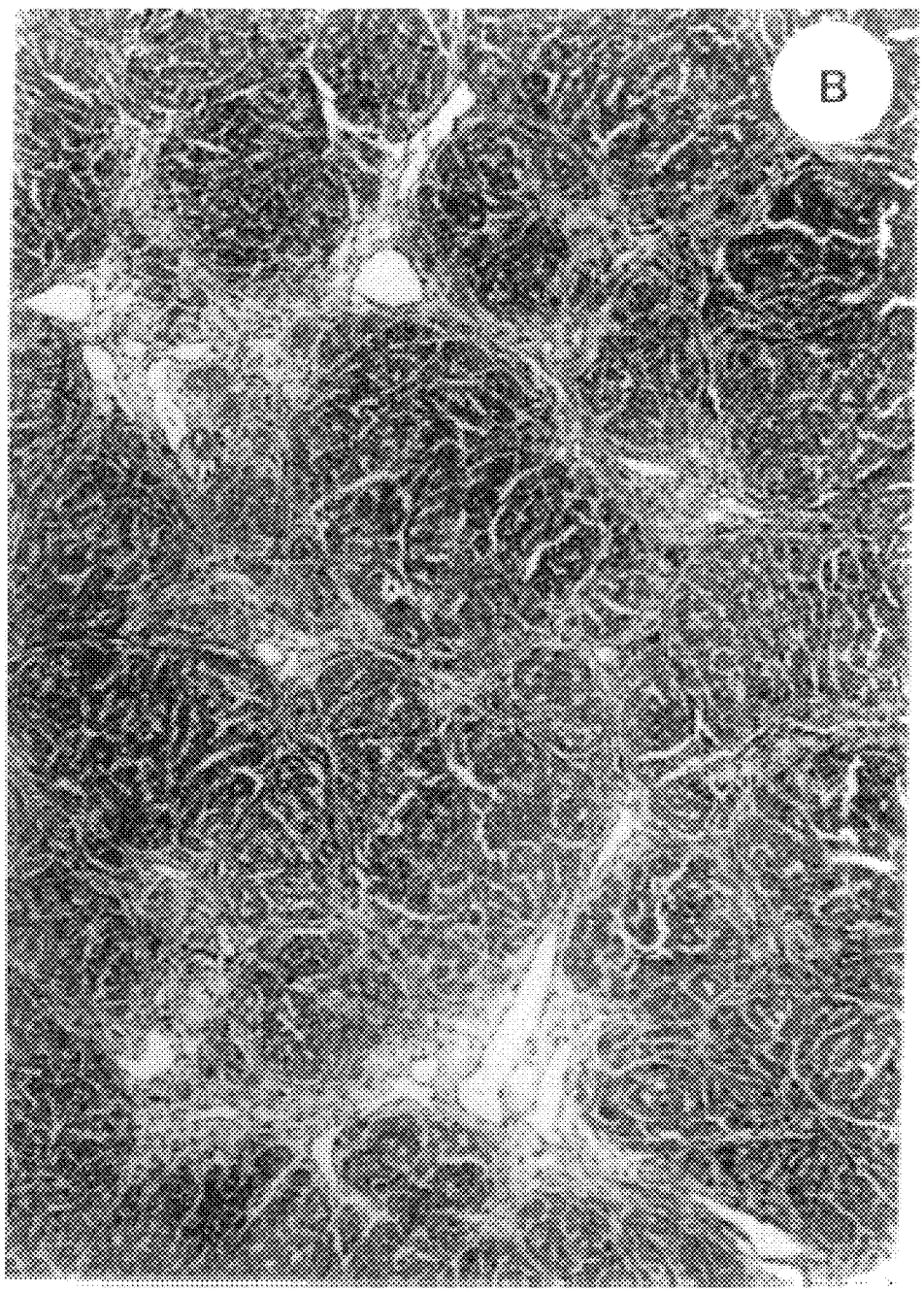
Figure 11C:
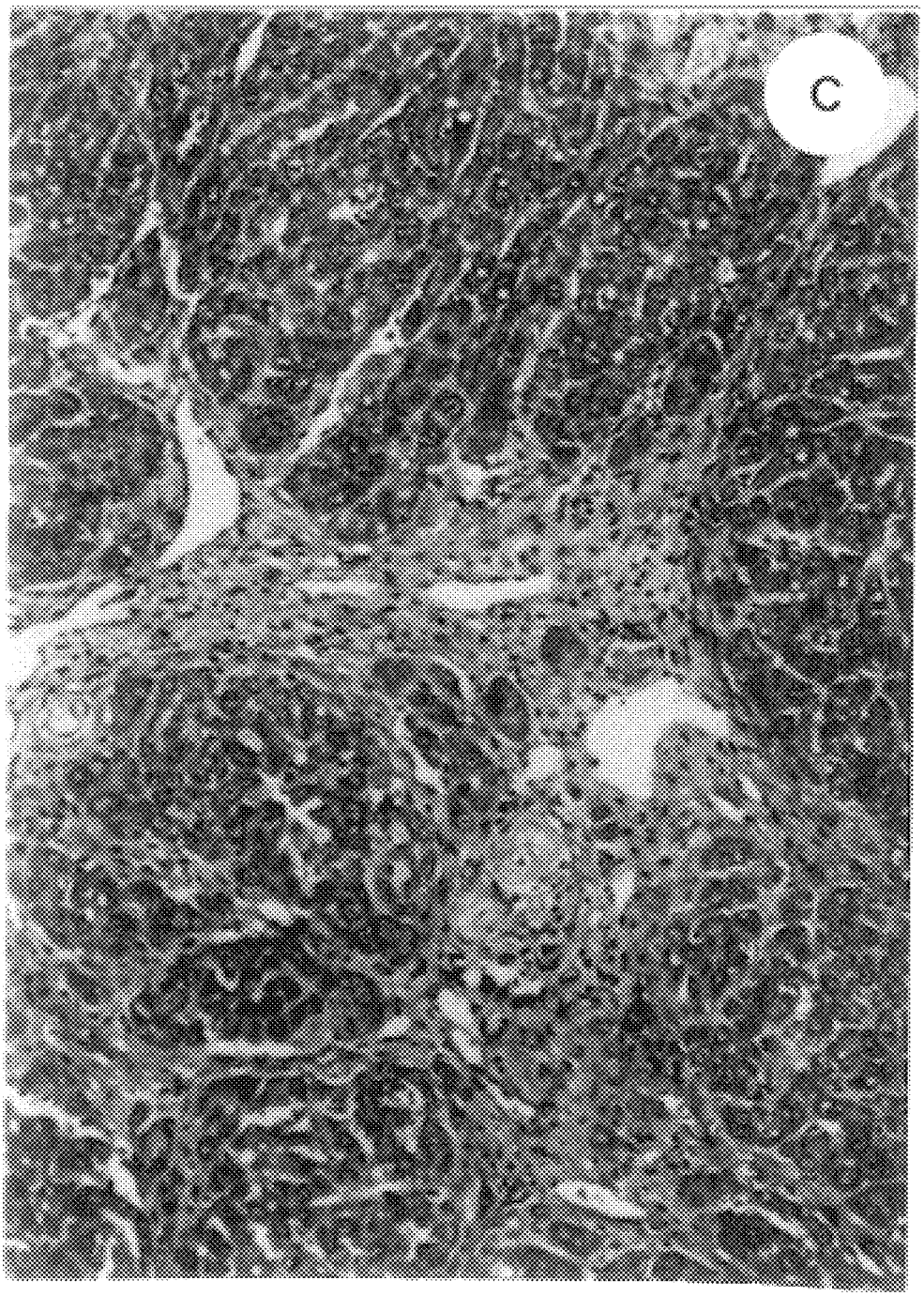
Figure 11D:
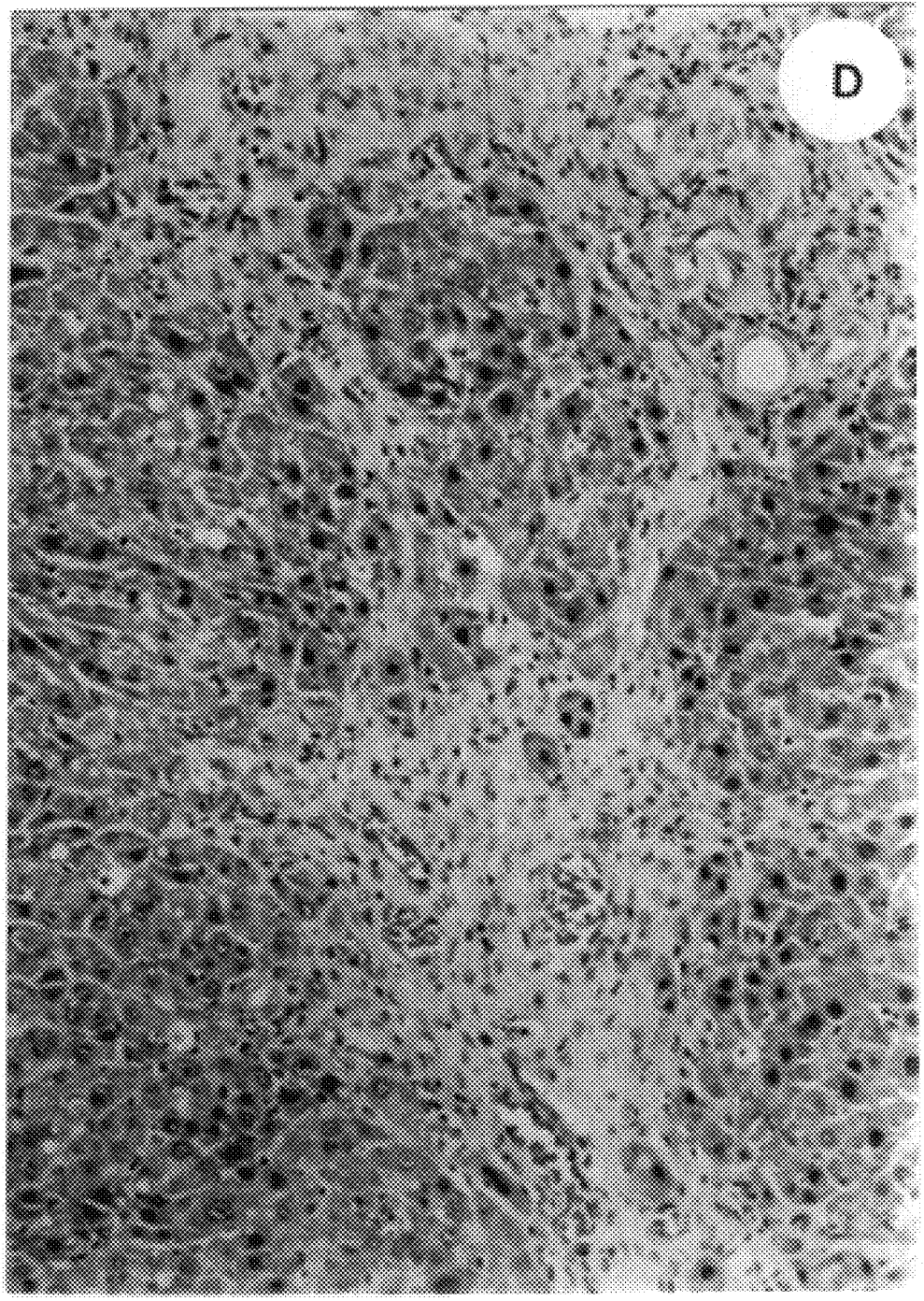
Figure 11E:
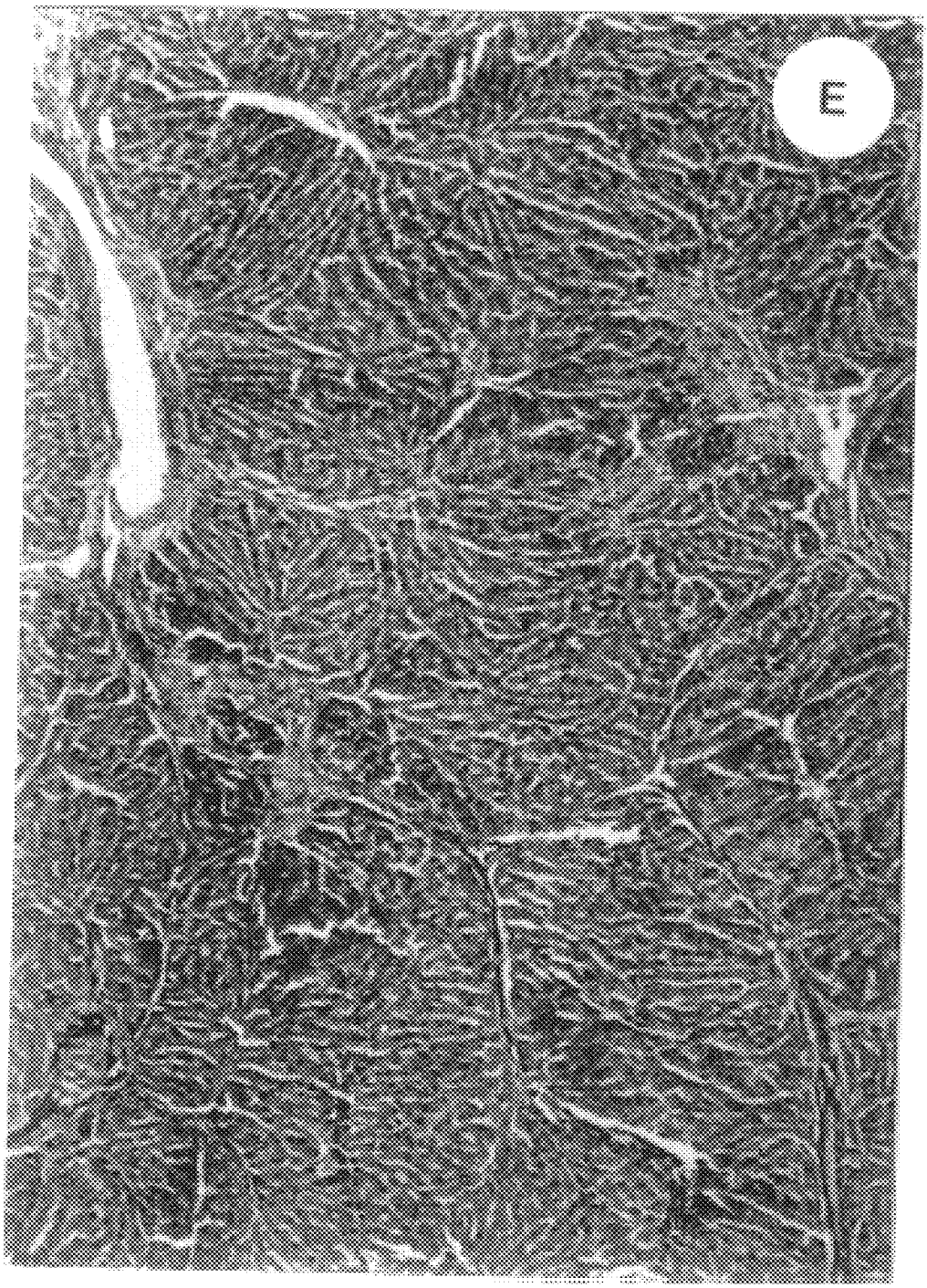
Figure 11F:
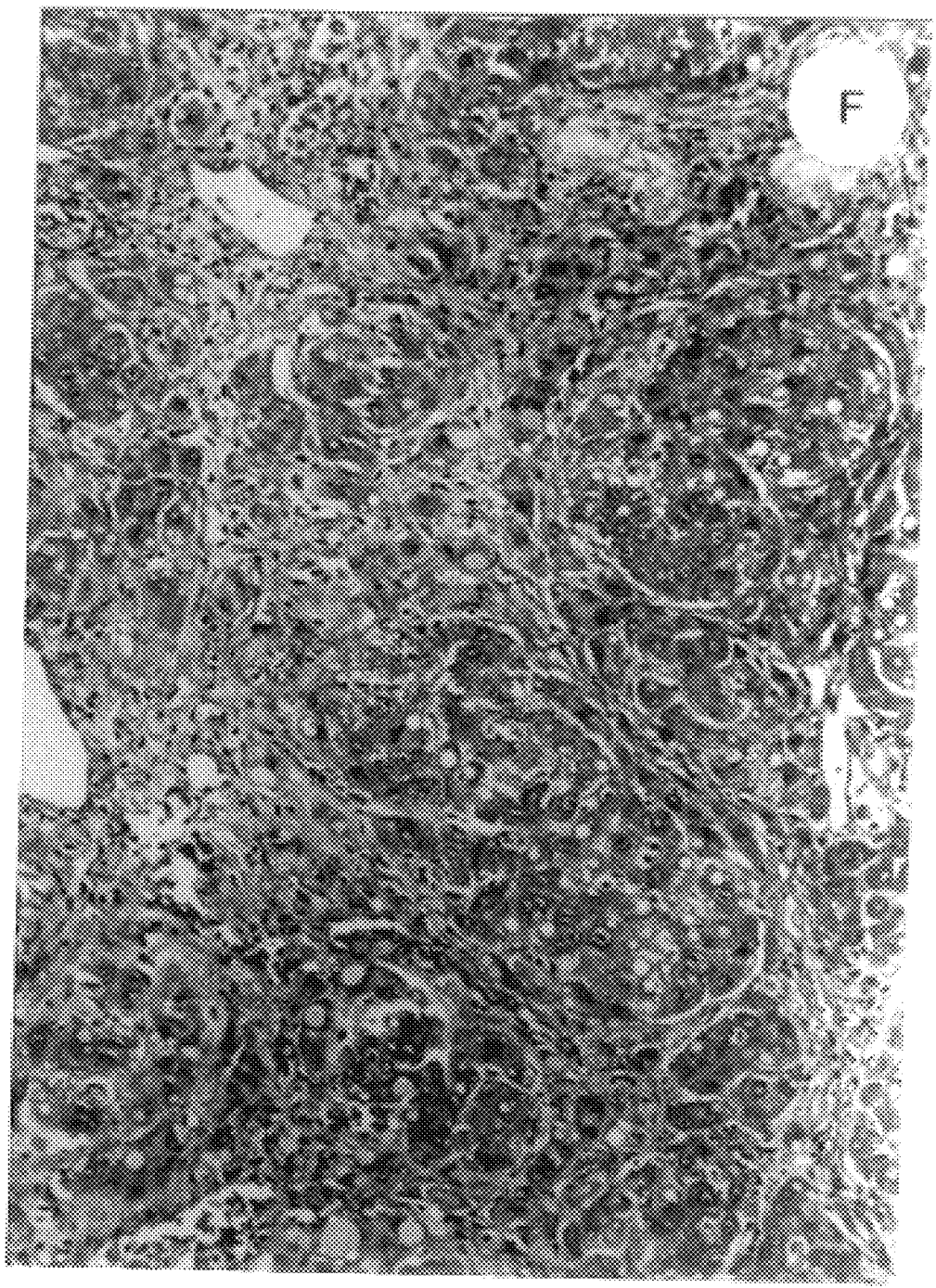

As can be seen from FIG. 10, when compared with the blood sample obtained from the rat treated with $CCl_4$, DMSO and PBS which was used as a control group, sGOT values of the blood samples obtained from the rats treated with each of methanol extract of *A. koreanum* Nakai($CCl_4$+A.M.) and acanthoic acid($CCl_4$+acan.) decreased by 20% and 30%, respectively. Further, sGPT values in the blood samples obtained from the rats treated with acanthoic acid ($CCl_4$+acan.) decreased more than 40%.

For the pathohistological examination of the livers separated from the above rats, the liver was fixed in 10% aqueous solution of neutral formalin, spread out in 4 mm thickness and then embedded in paraffin. The embedded tissue was sectioned in 5 mm thickness, stained with hematoxylin eosin and Masson's trichrome, and then observed under a microscope (FIG. 11).

As can be seen from FIG. 11, in the liver of the rat administered with $CCl_4$ only(B, C and D), the nodule formation of hepatic lobules with the relatively thickened fibrous bands is remarkable compared with the normal liver(A). In the liver of the rat administered with $CCl_4$ and methanol extract of *A. koreanum* Nakai(E), even though signs of hepatocirrhosis are shown, their fibrous bands surrounding the nodule of hepatic lobule are thinner than those of the liver obtained from the rat treated with $CCl_4$ only, many nodules are incomplete, and the regenerative change of hepatic cells decreases compared with that of the liver obtained from the rat treated with $CCl_4$ only. In the liver of the rat administered with $CCl_4$ and acanthoic acid (F), the inhibitory effect on the hepatocirrhosis is lower than that of E.

The following Formulation Example is for illustration only and not intended to limit the scope of the invention in any way.

FORMULATION EXAMPLE

Hard gelatin capsules were prepared using the following ingredients:

|                    | Quantity (mg/capsule) |
|--------------------|-----------------------|
| Active ingredient  | 20                    |
| Starch, dried      | 160                   |
| Magnesium stearate | 20                    |
| Total              | 200 mg                |

The above ingredients were mixed and filled into hard gelatin capsules in 200 mg unit quantities.

While the invention has been described with respect to the above specific embodiments, it should be recognized that various modifications and changes may be made and also fall within the scope of the invention as defined by the claims that follow.

What is claimed is:

1. A method for inhibiting the production of interleukin-1 or tumor necrosis factor-α in a patient in need thereof, which comprises administering a therapeutically effective amount of isolated and purified acanthoic acid to said patient.

2. A method for inhibiting collagen synthesis, production of reactive oxygen species, proliferation of fibroblast or uncontrolled increase in the serum GOT and/or GPT levels in a patient, which comprises administering isolated and purified acanthoic acid to said patient an amount effective to inhibit the production of interleukin-1 or tumor necrosis factor-α.

3. A method for treating a disease selected from the group consisting of rheumatoid arthritis, hepatocirrhosis and silicosis, which comprises administering isolated and purified acanthoic acid to a patient suffering from said disease in an amount effective to inhibit the production of interleukin-1 or tumor necrosis factor-α.

* * * * *